United States Patent
Zhang

(10) Patent No.: US 6,630,167 B2
(45) Date of Patent: Oct. 7, 2003

(54) HYALURONIC ACID ANTI-ADHESION BARRIER

(75) Inventor: Guanghui Zhang, Belle Mead, NJ (US)

(73) Assignee: United States Surgical Corporation, Norwalk, CT (US)

(*) Notice: Subject to any disclaimer, the term of this patent is extended or adjusted under 35 U.S.C. 154(b) by 12 days.

(21) Appl. No.: 10/036,239

(22) Filed: Dec. 28, 2001

(65) Prior Publication Data

US 2002/0141968 A1 Oct. 3, 2002

Related U.S. Application Data

(60) Provisional application No. 60/146,065, filed on Jul. 28, 1999.

(51) Int. Cl.[7] ............................. A61K 9/14; A61K 31/74; C08J 9/00
(52) U.S. Cl. ................. 424/484; 424/78.02; 424/78.38; 424/400; 521/82; 521/84.1; 521/92; 521/134; 521/138
(58) Field of Search ............................. 424/484, 78.02, 424/78.38, 400; 514/54; 527/301; 536/53; 521/82, 84.1, 92, 134, 138

(56) References Cited

U.S. PATENT DOCUMENTS

| | | | |
|---|---|---|---|
| 3,682,174 A | 8/1972 | Cohen | 128/220 |
| 4,141,973 A | 2/1979 | Balazs | 424/180 |
| 4,517,295 A | 5/1985 | Bracke et al. | 435/101 |
| 4,582,865 A | 4/1986 | Balazs et al. | 524/29 |
| 4,636,524 A | 1/1987 | Balazs et al. | 514/781 |
| 4,716,224 A | 12/1987 | Sakurai et al. | 536/55.1 |
| 4,886,787 A | 12/1989 | De Belder et al. | 514/57 |
| 4,957,744 A | 9/1990 | Della Valle et al. | 424/401 |
| 5,356,883 A | 10/1994 | Kuo et al. | 514/54 |
| 5,532,221 A | 7/1996 | Huang et al. | 514/53 |
| 5,690,961 A | 11/1997 | Nguyen | 424/488 |
| 5,840,777 A | * 11/1998 | Eagles et al. | 521/82 |

OTHER PUBLICATIONS

Meyers, Physiol. Rev., 27:335, 1947.

* cited by examiner

*Primary Examiner*—Thurman K. Page
*Assistant Examiner*—Blessing Fubara

(57) ABSTRACT

Methods of forming crosslinked hyaluronic acid anti-adhesion barriers, crosslinked hyaluronic acid anti-adhesions barriers, methods for preventing or inhibiting adhesions, and methods of promoting healing of a wound are provided. The method of forming the crosslinked hyaluronic acid anti-adhesion barrier includes freeze-drying a solution including hyaluronic acid to form a hyaluronic acid foam, which is then reacted with a crosslinking agent to form a crosslinked hyaluronic acid foam. The crosslinked hyaluronic acid foam is mixed with a solution containing hyaluronic acid to form an anti-adhesion barrier.

37 Claims, 3 Drawing Sheets

HYALURONIC ACID ANTI-ADHESION BARRIER

This application claims benefit of provisional application Serial No. 60/146,065 filed Jul. 28, 1999.

BACKGROUND

1. Technical Field

The present disclosure relates to a method of preparing an anti-adhesion barrier from hyaluronic acid, to the anti-adhesion barrier formed thereby, and to methods of using the anti-adhesion barrier.

2. Background of the Related Art

Hyaluronic acid is a viscous mucopolysaccharide found in animal and human tissues such as the umbilical cord, vitreous humor, synovial fluid, blood vessel walls and other connective tissues. The polysaccharide consists of repeating disaccharide units made of alternating D-glucuronic acid and N-acetyl-D-glucosamine residues, and possesses a molecular weight ranging from about 40,000 to 8,000,000 depending on the source and methods of extraction. Hyaluronic acid is found in between cells complexed with proteins, and forms a jelly due to its ability to retain water. It plays an important role in various biological processes, such as cell migration, lubrication, moistening of tissues, and maintenance of cell morphology (Meyers, Physiol. Rev., 27: 335, 1947).

Its natural occurrence in the body and its ability to retain water have lead to the development and use of hyaluronic acid for various therapeutic applications, e.g., the treatment of arthritis, the use of hyaluronic acid as a vitreous humor substitute, the prevention or inhibition of adhesions following surgery, and the protection of wounds during healing. However, upon administration to an individual, hyaluronic acid undergoes enzymatic degradation by various enzymes, e.g., hyaluronidase, glucoronidase, and glucosidase, or non-enzymatic degradation (Pigman et al., Arthritis Rheumatism 4: 240, 1961), and thus does not maintain its original viscosity or desired residence time in vivo.

One successful approach to delay degradation of hyaluronic acid when administered to the body, and thus preserve its original viscosity and residence time in vivo, has been to modify hyaluronic acid with a crosslinking agent. Various crosslinking agents and methods have been utilized to crosslink hyaluronic acid for use in various therapeutic applications. For example, U.S. Pat. No. 4,716,224 describes the crosslinking of hyaluronic acid with the use of poly-functional epoxy compounds wherein the hyaluronic acid is dissolved and reacted with the epoxy compounds in an alkaline medium. The crosslinked hyaluronic acid is described as useful in the treatment of arthritis and as an ingredient of cosmetics.

U.S. Pat. No. 4,886,787 describes crosslinking hyaluronic acid with di or polyfunctional epoxides wherein the hyaluronic acid is dissolved and reacted with the epoxides in an acidic solution, in the presence of an acidic catalyst. The crosslinked hyaluronic acid is proposed to be useful in the treatment of arthritis, as a drug delivery vehicle, to reduce post-operative adhesions, to promote wound healing, and as a component of cosmetics.

U.S. Pat. Nos. 4,582,865, 4,605,691 and 4,636,524 describe the reaction of divinyl sulfone as crosslinking agent with hyaluronic acid in an aqueous alkaline solution. The crosslinked hyaluronic acid is described as being useful in cosmetic formulations and drug delivery systems.

U.S. Pat. No. 5,356,883 describes crosslinking hyaluronic acid with the crosslinking agent carbodiimides to produce hydrogels which are purportedly useful as biocompatible gels, films or sponges.

U.S. Pat. No. 4,957,744 describes crosslinking hyaluronic acid with polyhydric alcohols to produce crosslinked hyaluronic acid esters, which are described as useful for treatment of arthritis, and as components of cosmetics. The crosslinking reaction is effected by dissolving and reacting hyaluronic acid with a crosslinking agent in polar and non-polar solvents.

U.S. Pat. No. 5,690,961 describes crosslinking hyaluronic acid with di- or polyanhydrides in a polar, aprotic solvent. The anhydride-crosslinked hyaluronic acid is proposed to be useful in the treatment of arthritis, as a drug delivery vehicle, to reduce the formation of post-operative adhesions, to promote wound healing and as an ingredient in cosmetics.

U.S. Pat. No. 5,532,221 describes the production of ionically-crosslinked hyaluronic acid, wherein an aqueous solution of hyaluronic acid is contacted with an aqueous polycation solution. The ionically-crosslinked hyaluronic acid is described as useful in preventing post-operative adhesions.

In the literature described above, regardless of the particular crosslinking agent used, the crosslinking of hyaluronic acid is carried out in a homogenous solution state, wherein hyaluronic acid is dissolved and reacted with the crosslinking agent in a solution. Since the solubility of hyaluronic acid in aqueous solution is very low, the reactions carried out in such homogenous solutions are not efficient. Accordingly, recovery of the reaction product can be difficult.

SUMMARY

A method of forming an anti-adhesion barrier is provided which comprises freeze-drying a solution including hyaluronic acid to form a foam, reacting the foam with a crosslinking agent to form a crosslinked foam and mixing the crosslinked foam with an aqueous solution containing hyaluronic acid to form the anti-adhesion barrier.

In another aspect, an anti-adhesion barrier is provided which is a gel produced by combining a freeze-dried crosslinked hyaluronic acid foam and an aqueous solution including hyaluronic acid.

In yet another aspect, a two-part kit is provided which comprises a first part including freeze-dried crosslinked hyaluronic acid foam, and a second part including a solution including hyaluronic acid.

As stated previously, prior art methods for preparing crosslinked hyaluronic acid, in general, involve a crosslinking step which is performed in a homogenous solution state, i.e., hyaluronic acid is dissolved and reacted with a crosslinking agent in a solution. In contrast, the present method of preparing an anti-adhesion barrier involves a unique solid-state crosslinking reaction wherein hyaluronic acid is prepared as a solid, i.e., freeze-dried foam, which is then reacted with a neat liquid crosslinking agent to yield a crosslinked hyaluronic acid foam. This method eliminates the concern of low solubility of hyaluronic acid in various solvents. Also, because the crosslinking agents only react with those functional groups accessible on surfaces, the use of a freeze-dried hyaluronic acid foam provides a relatively large surface area containing sites at which crosslinking can occur.

The production of crosslinked hyaluronic acid foam in accordance with the method of the present invention results in a near-quantitative recovery of crosslinked hyaluronic acid foam. The excess crosslinking agents and any reaction by-products can be easily removed by simple washing. In contrast, recovery of crosslinked hyaluronic acid produced by the methods of the prior art wherein crosslinking is conducted in homogenous solution state is less efficient and removal of excess crosslinking agents and reaction by-products is more time consuming.

BRIEF DESCRIPTION OF THE DRAWINGS

FIG. 2A shows two separate syringes containing crosslinked hyaluronic acid foam, and an aqueous solution containing hyaluronic acid, and a luer lock which is used for coupling the two syringes.

DETAILED DESCRIPTION OF PREFERRED EMBODIMENTS

Figure 1:
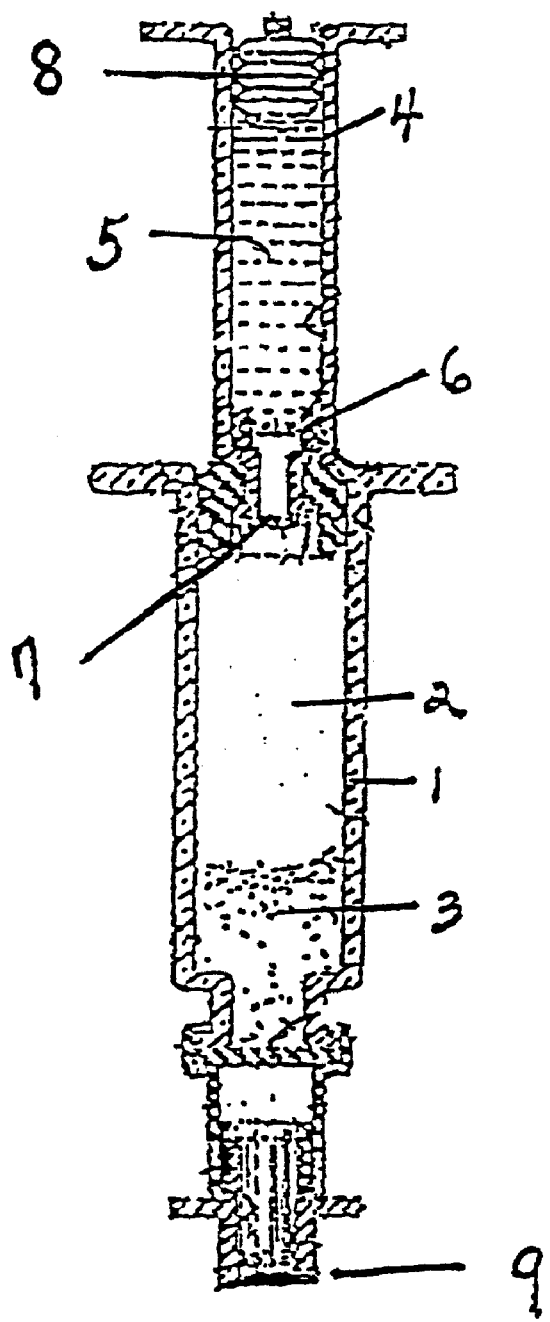
FIG. 1 is an example of a needleless syringe that can be utilized to mix hyaluronic acid foam with an aqueous solution containing hyaluronic acid to form the anti-adhesion barrier.

The presently disclosed method of forming an anti-adhesion barrier includes a novel crosslinking step wherein a freeze-dried hyaluronic acid foam is reacted with a crosslinking agent to produce a crosslinked hyaluronic acid foam, which is then mixed with an aqueous solution comprising hyaluronic acid to form a hydrogel anti-adhesion barrier.

As used herein, the term "hyaluronic acid" refers to hyaluronic acid and its salts such as the sodium, potassium, calcium or magnesium, etc., salts. To form an anti-adhesion barrier as set forth in the presently claimed method, hyaluronic acid or a biocompatible salt thereof, e.g., sodium, potassium, calcium or magnesium, is dissolved in an aqueous solution, which is preferably pyrogen-free. The molecular weight of hyaluronic acid may range from about 40,000 to 8,000,000 depending on the source and the purification methods utilized. Suitable sources of hyaluronic acid include, but are not limited to, umbilical cord, rooster comb, bacteria, etc. For example, U.S. Pat. No. 4,141,973, the contents of which are incorporated by reference herein describes a method for extracting hyaluronic acid from rooster combs, and U.S. Pat. No. 4,517,295, the contents of which are incorporated by reference herein describes a fermentation method for preparing hyaluronic acid. Hyaluronic acid is also commercially available, e.g., from Genzyme Corp., Cambridge, Mass. and Sigma Chemical Co., St. Louis, Mo.

The molecular weight of hyaluronic acid affects the amount of hyaluronic acid that is required to achieve gel formation. Accordingly, the concentration of hyaluronic acid used to form a foam in the present method will be adjusted according to the molecular weight of the hyaluronic acid utilized. For example, when using a higher molecular weight hyaluronic acid, a lower concentration of hyaluronic acid is required to achieve gel formation. Typically, when using hyaluronic acid having a molecular weight of about $1 \times 10^6$ to about $2 \times 10^6$, the solution including hyaluronic acid will contain from about 0.5 to about 4.0% by weight hyaluronic acid.

The solution including hyaluronic acid is then frozen, preferably flash-frozen at a temperature of from about −94 to about −130° C. by, e.g., immersing a flask containing the solution including hyaluronic acid in an acetone-dry ice bath. By flash-freezing the solution including hyaluronic acid, a porous hyaluronic acid foam can be obtained upon freeze-drying the frozen solution including hyaluronic acid. Formation of a foam increases the surface area that is exposed to crosslinking reagent. The formation of a porous foam allows crosslinking agent to reach all the surface area. The frozen hyaluronic acid solution is freeze-dried, preferably at a temperature of from about 0 to about −10° C. and at a pressure of from about $50 \times 10^{-3}$ to about $1 \times 10^{-3}$ torr to form a porous foam.

Subsequently the foam is reacted with a liquid crosslinking agent to produce crosslinked foam. Suitable crosslinking agents are well-known in the art, and include but are not limited to, di-epoxides, poly-functional epoxides, diisocyanates, polyisocyanates, polyhydric alcohols, water-soluble carbodiimides, diamines, diaminoalkanes, polycarboxylic acids, diacid halides, and dimethylol urea. Preferably, the crosslinking agent is a diacid halide which includes, but is not limited to, diglycolyl chloride, adipoyl chloride, and sebacyl chloride. More preferably, the diacid halide is diglycolyl chloride. The crosslinking agent can be a liquid or rendered liquid, if necessary by dissolving the crosslinking agent in a suitable solvent, e.g., methylene chloride, or N,N-dimethylformamide. When a solvent is used, the concentration of crosslinking agent is from about 1.0 to about 99.0% by weight, preferably from about 10 to about 80 weight percent of the solution. It is preferred in the practice of the present invention to employ substantially pure crosslinking agents.

To effect crosslinking, the foam is immersed in the liquid crosslinking agent and stirred for an appropriate period of time, usually for about 24 to about 48 hours. The reaction is usually performed at room temperature, i.e., at about 23° C., however, the temperature at which the crosslinking reaction is conducted is not critical.

The ratio of foam to crosslinking agent is from about 3.0 to about 100 grams foam/gram crosslinking agent.

When a diacid halide is employed as crosslinked agent, an acid scavenger, e.g., triethylamine, can be also added to the crosslinking reaction mixture to neutralize the hydrochloric acid that is formed during the crosslinking reaction. The crosslinked foam is washed a few times to remove any unreacted crosslinking agent, dried under vacuum and sterilized.

Subsequently, the crosslinked foam is mixed with a sterilized aqueous solution which contains from about 0.5 to about 4.0% by weight hyaluronic acid, and preferably at about 2.0% by weight hyaluronic acid. Typically, the ratio of crosslinked foam to aqueous solution containing hyaluronic acid employed in the mixture ranges from about 0.2 to about 1.0 gram crosslinked foam/ml hyaluronic acid solution. When the crosslinked foam is crosslinked with diglycolyl chloride, generally, the aqueous solution containing hyaluronic acid which contains from about 0.5 to about 2.0% by weight hyaluronic acid is mixed with the crosslinked foam. The proportion of foam crosslinked with diglycolyl chloride to the hyaluronic acid solution is preferably 0.2 grams crosslinked hyaluronic acid foam/ml of a hyaluronic acid solution containing 1.0% by weight hyaluronic acid.

The crosslinked hyaluronic acid foam and solution may be mixed by any convenient method. For example, the foam and solution may each be placed in a syringe coupled with a luer lock, and the contents of each syringe mixed by pushing the plungers back and forth. The resulting hydrogel anti-adhesion barrier can then be collected in one of the syringes.

The anti-adhesion barrier is biodegradable and is thus reabsorbed over a period of time, obviating the need for subsequent surgery to remove the barrier. The rate of degradation of the anti-adhesion barrier can be controlled by increasing the degree of crosslinking.

In another aspect, the anti-adhesion barrier can be used to prevent or inhibit the formation of adhesions in an animal following any type of surgery or trauma, by applying an effective amount of the anti-adhesion barrier described above to a wound site. The wound site refers to a site of tissue that has been injured in any manner, e.g., through surgery, contusion, abrasion, and so forth, and also refers to tissues or organs that are adjacent to the injured tissue. For example, the barrier may be used to prevent or inhibit adhesions that form in relation to intestinal surgery, e.g., bowel resection, hernia repair, etc., which may cause obstruction of the intestine. The barrier may also prevent or inhibit adhesions that form near a bone fracture site which may reduce or hinder the normal movement of the area of repair by restricting the natural movement of tendons over adjacent bone.

An effective amount of an anti-adhesion barrier is that amount required to prevent or inhibit adhesions. Preferably, the amount should be sufficient to coat the entire wound site. An additional amount may also be applied to body tissues or organs adjacent to the wound site. The effective amount can be determined readily by one skilled in the art.

In one embodiment, as described above, the crosslinked foam and hyaluronic acid solution are mixed outside of the body to form a hyaluronic acid anti-adhesion barrier. The barrier is then applied to the wound site by any convenient mode. Preferably, the anti-adhesion barrier is applied directly to the wound site by injection through a needleless syringe as set forth in Example 2.

In another aspect, the barrier may be used to promote healing of a wound by applying an effective amount of the barrier described above to the wound. An additional amount may also be applied to the body tissue adjacent to the wound. The effective amount can be determined readily by one skilled in the art.

The barrier is administered to the wound by any convenient mode, e.g., by applying the gel directly to the wound, or the gel may be combined with a wound dressing or bandage that is applied to the wound, or any other convenient mode.

The anti-adhesion barrier used to prevent or inhibit adhesions, or promote healing of a wound as described above may be included in compositions with a pharmaceutically acceptable carrier, e.g., water or a nonaqueous solvent, and/or at least one medicinal agent. Suitable medicinal agents may be included in the compositions by adding the medicinal agent to the hyaluronic acid solution prior to mixing the solution with the crosslinked foam to form the anti-adhesion barrier, or after formation of the anti-adhesion barrier.

The term "medicinal agent", as used herein, is meant to be interpreted broadly and includes any substance or mixture of substances which may have any clinical use in medicine. Thus, medicinal agents include drugs, enzymes, proteins, peptides, glycoproteins, or diagnostic agents such as releasable dyes which may have no biological activity per se.

Examples of classes of medicinal agents that can be used include antimicrobials, analgesics, antipyretics, anesthetics, antiepileptics, antihistamines, anti-inflammatories, anti-clotting agents, cardiovascular drug, diagnostic agents, sympathomimetics, cholinomimetics, anti-muscarinics, antispasmodics, hormones, growth factors, muscle relaxants, adrenergic neuron blocks, anti-neoplastics, immunosuppressants, gastrointestinal drugs, diuretics, steroids and enzymes. It is also intended that combinations of medicinal agents can be used.

By incorporating a medicinal agent(s) into the hyaluronic acid anti-adhesion barrier of this invention, focal delivery and application of a medicinal agent(s) to a wound is achieved. Focal application of growth factors, anti-inflammatories, immune system suppressant and/or antimicrobials by the anti-adhesion barrier is an ideal drug delivery system to speed healing of a wound or incision. Delivery of suitable anti-clotting agents in prevent fibroblast formation, thus augmenting the effect of the physical barrier in preventing or inhibiting adhesions. The medicinal agent(s) diffuse from the hydrogel barrier and/or are released as the barrier is biodegraded and absorbed.

In another aspect, a two-part kit is provided which includes a first part including a freeze-dried crosslinked hyaluronic acid foam, and a second part including a solution including hyaluronic acid. The kit can also include at least one medicinal agent as described above, which may be included separately from the other components in the kit, or may be added to the solution including hyaluronic acid supplied in the kit. The kit can also include any convenient means for mixing the crosslinked hyaluronic acid foam with the solution including hyaluronic acid.

One example of a means for combining the crosslinked hyaluronic acid foam with the aqueous solution containing hyaluronic acid is a modified version of the syringe described in U.S. Pat. No. 3,682,174, which is incorporated herein by reference. With reference to FIG. 1, the modified syringe, i.e., needleless syringe, includes an outer casing 1 of a tubular member having a bore 2, which hold the powdered substance 3, i.e., hyaluronic acid foam. A second tubular member 4 holds the liquid 5, i.e., an aqueous solution containing hyaluronic acid. The powdered substance 3 is sealed off from the second tubular member using a floating sealing member 6 and a sealing member 7. Thus, the powder contained in the first member is completely separated from the second member. When an actuator (not shown in this figure) connected to the top portion of the syringe is pressed down, the plug 8 is displaced, which in turn, places the liquid 5 under pressure. The sealing member 7 becomes distorted, allowing the liquid to flow into the bore 2 of the first tubular member. The liquid mixes with the powder, with shaking if required, to provide a freshly prepared suspension, i.e., a gel anti-adhesion barrier. The gel is held in place by a covering 9 which is secured to the bottom portion of the syringe. The covering is removed to allow the gel to be dispersed and administered to the desired site.

Figure 2A:
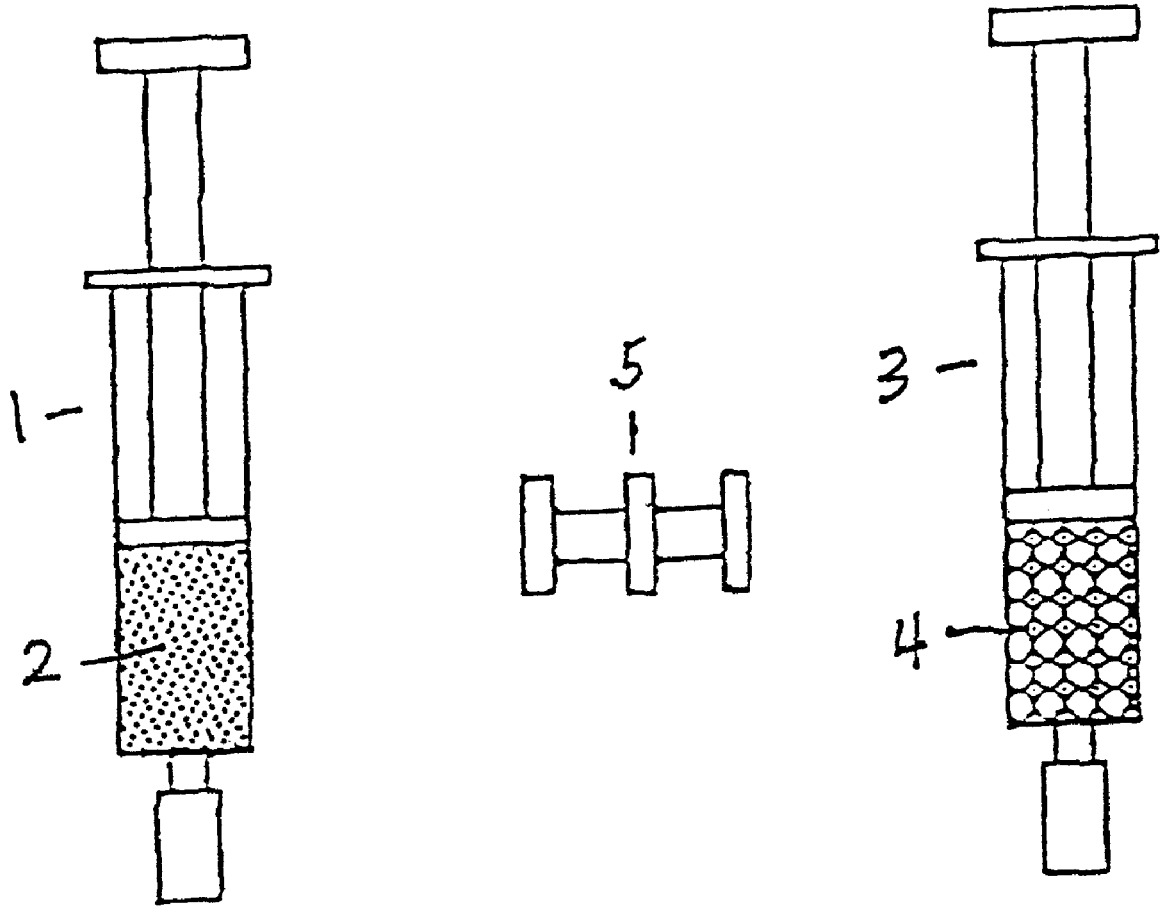
FIGS. 2A and B shows two needleless syringes and a luer lock that can be used to mix an aqueous solution containing hyaluronic acid and crosslinked hyaluronic acid foam to form an anti-adhesion barrier.
Figure 2B:
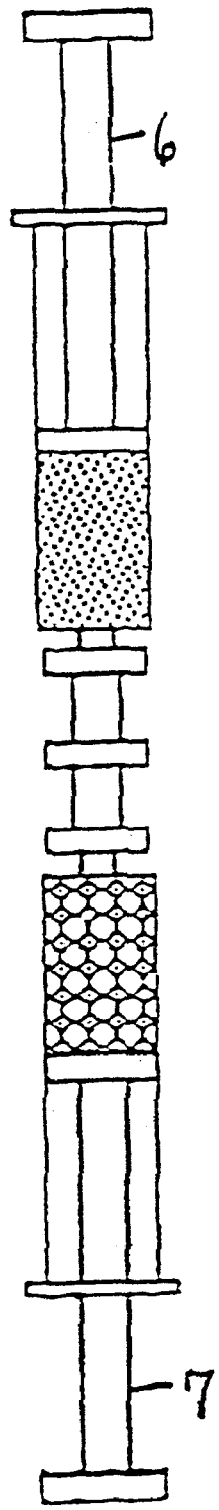
FIG. 2B shows the syringes coupled via a luer lock. The liquid and solid components are mixed by pushing the plungers back and forth to form a gel. The gel is collected in one of the syringes prior to its application to a wound site.

In a second example, the crosslinked hyaluronic acid foam and hyaluronic acid solution are mixed by placing each in a separate needleless syringe which is coupled to a luer lock as described above, followed by mixing of the contents. With reference to FIG. 2A, the syringe 1 contains an aqueous solution of hyaluronic acid 2 and syringe 3 contains a crosslinked hyaluronic acid foam 4. The luer lock 5 is used for coupling syringe 1 to syringe 3. FIG. 2B shows the coupling of syringe 1 to syringe 3 using the luer lock 5. The aqueous solution of hyaluronic acid 2 and the crosslinked hyaluronic acid foam 4 are mixed by pushing the plungers 6 and 7 back and forth to form the gel anti-adhesion barrier. Before applying the gel to a wound site, it is collected in either syringe 1 or syringe 3.

In order that those skilled in the art may be better able to practice the present invention, the following examples are given as illustrations of the preparation of an anti-adhesion barrier, and methods of use thereof in accordance with the present disclosure. It should be noted that the invention is not limited to the specific details embodied in the examples.

EXAMPLE 1

A. Preparation of Hyaluronic Acid Foam

Cosmetic grade hyaluronic acid (5.0 g) (Genzyme Corp., Cambridge, Mass.) was dissolved in distilled water (1000 ml). The hyaluronic acid solution (0.5%) was stirred at room temperature for approximately 12 hours. Hyaluronic acid (125 ml) solution was added to a 250 ml flask, followed by rapidly freezing the solution at about 94° C., by immersing the flask in an acetone/dry ice bath. The frozen solution was then placed in a lyophilizer, at a vacuum of less than 1 torr for 3 to 4 days, to form a hyaluronic acid foam.

B. Preparation of Diglycolyl Chloride Solution

A 3 necked round-bottomed flask (2 liter) fitted with a 300 ml addition funnel and a condenser with hydrogen flow was charged with diglycolic acid (100 g) and toluene (1000 ml), followed by addition of N, N-dimethylformamide (1–2 ml), a catalyst. From the addition funnel, thionyl chloride (275 ml) was added dropwise to the round bottomed flask while stirring. The mixture was heated to 50° C., and then kept heated overnight. The reaction was then allowed to continue at room temperature for two days. The toluene and thionyl chloride were distilled off at 50° C. under a vacuum, followed by heating the mixture at 80° C. under a vacuum. The diglycolyl chloride was collected in a receiving flask. Upon distillation, the diglycolyl chloride (125 g) turned into a pinkish liquid. Nuclear Magnetic Resonance confirmed that all of the toluene was distilled off.

C. Preparation of Crosslinked Hyaluronic Acid Foam

Hyaluronic acid foam (0.325 g) prepared in Step A was immersed in a beaker containing diglycolyl chloride (100 g) which was prepared in step B. Triethylamine (1.0 ml) was added dropwise to the beaker to neutralize any hydrochloric acid that was generated during the crosslinking reaction, and the mixture was stirred for 24 hours at room temperature. The crosslinked foam was then separated from diglycolyl chloride using a sintered glass funnel. The collected crosslinked foam was washed three times with 200 ml of isopropanol to remove unreacted diglycolyl chloride, followed by a wash with 200 ml of ethanol. The washed crosslinked foam was then dried under vacuum at −40° C. for 24–48 hours to yield approximately 0.3 grams of crosslinked hyaluronic acid foam.

D. Formulation and Delivery of the Crosslinked Hyaluronic Acid Gel

The crosslinked hyaluronic acid foam was sterilized by ethylene oxide and a 1% hyaluronic acid solution was sterilized by steam for 120 minutes at 121° C. Under aseptic conditions, hyaluronic acid foam (0.2 g) was packed into a sterile 3 cc syringe, and hyaluronic acid solution (1 ml) was added to another syringe. Both syringes were uncapped, coupled with a luer lock, and the contents of each syringe were mixed by pushing the plungers back and forth. The gel was collected in one of the syringes, and then delivered to the surgical site.

EXAMPLE 2

Crosslinked Hyaluronic Acid Gel Employed as Anti-Adhesion Barrier in Rats

The ability of the crosslinked hyaluronic acid gel of Example 1 to prevent or inhibit the formation of post-surgical adhesions was examined using a standardized rat abdominal adhesion model.

The test materials employed in the model were as follows:

Hyaluronic Acid Gel, 8 individually sealed packages, each containing two syringes with the separate components for a single (or half) application of gel (mixed prior to surgery).

The wet and dry components of the hyaluronic acid gel kit were mixed prior to use using a syringe coupler to aerate and combine the components as they were passed from one syringe to the other. The mixed gel was transferred to one of the syringes for application. In 3 animals, the entire contents of the syringe was applied to the abdominal wall defect (AWD), completely coating it with a 5 mm margin beyond each edge of the defect. In 5 animals only half of the volume of the gel was applied to the AWD of each animal. In all animals saline was dripped onto the exposed surface of the gel.

Female Sprague-Dawley rats (225–249 grams) were utilized in this experiments. Each animal received a 2×1 cm surgical defect on the peritoneal surface of their right abdominal wall, and a similar sized defect on their cecum. The animals were divided into two treatment groups. In the first group, the AWD was covered by a layer of hyaluronic acid gel. The animals in the second group served as controls with no treatment applied to either defect. All animals were sutured closed and bandaged.

The details of the model are described in Surgery 117: 663–9, 1995, the contents of which are incorporated by reference herein. In brief, the animals were anesthetized with sodium pentobarbital (43 mg/kg intraperitoneal), their abdomens were shaved, and a 6 cm incision line was marked on the skin overlying the linear alba on the ventral midline. The skin was prepped with iodophor solution, rinsed with 70% isopropyl alcohol, and incised. With the muscle wall exposed, a 5 cm incision in the muscle was made along the linear alba through to the peritoneal cavity. The right abdominal wall was reflected, and a 2 cm×1 cm surface was denuded by removing the peritoneum and some associated muscle fibers. The medial edge of this defect was located parallel to, and 1 cm lateral to the midline incision. The contents of the cecum were removed by milking the material away from the terminal end of the cecum.

A defect was created on the cecum by rubbing a moistened gauze pad on the surface of the cecum until a 2 cm×1 cm area of the serosal sheath covering the cecum was peeled away. Both the abdominal wall and the cecum were lightly scraped with a #15 scalpel blade to promote petechial bleeding, then exposed and allowed to air dry for 15 minutes. The non-defect areas of the abdominal wall and cecum were protected from drying by placing moist gauze over them during the drying period.

The prepared hyaluronic acid gel was quickly applied through the (needleless) syringe to the abdominal wall defect. An excess margin of gel was extended beyond the defect area at least 5 mm. The abdominal wall was closed with a running 4/0 polypropylene suture, and the skin was closed with a running 4/0 absorbable suture. The rats were bandaged and returned to their cages after anesthetic recovery.

The presence of adhesion formation between the cecum and the peritoneal wall was assessed 7 days following surgery. The animals were euthanized immediately prior to analysis. The skin and muscle layers of the abdomen were incised lateral and distal to the location of the original defects. The resulting U-shaped flap was slowly lifted to reveal the adhesion, if present. After carefully noting and separating any extraneous adhesions (i.e., retroperitoneal fat, bowel, omentum, etc.), two large silk suture loops were placed in the terminal end of the cecum. This permitted the eecum to be attached to a strain gauge mounted on the lead screw of a tensiometer. The caudal edge of the U-shaped flap was secured in a pin clamp such that the peritoneal wall was approximately 40–45° from the horizontal. As the lead screw was advanced at 8.8 cm/min., the cecum was peeled off the peritoneal defect. The force required to remove the cecum was plotted against time on a calibrated x-y recorder. After the two defect surfaces were separated, the length and width of the peritoneal area involved in the adhesion were measured with a caliper.

The following values were calculated for every animal with an adhesion: area of adhesion, percent of complete adhesion formation, maximum strength encountered during separation, maximum width of adhesion, average strength of separation, work to separate, and a normalized work value. The normalized work value was calculated because the work to separate each adhesion is related to adhesion area. Therefore, each work value was normalized to the work that would have been required if the entire surface had been involved in the adhesion by dividing the actual work by the actual percentage of surface involved.

In order to calculate work and normalized work, the area of each force-time curve on the x-y recorder was measured with a planimeter, multiplied by a factor converting curve height to force in grams, and divided by the curve length to obtain a value of average force in grams for each adhesion. The work to pull the adhesion was calculated using the formula W=$\underline{F}$·d, where W=work, $\underline{F}$=the average force, and d=the measured length of the peritoneal area involved in the adhesion. The normalized work was then calculated as the work, W, divided by the percentage of complete adhesion formation. When reported, forces were converted from grams to Newtons (N) using the acceleration due to gravity.

The results are summarized in Table 1.

TABLE 1

Incidence of adhesion formation at 7 days between an abdominal wall wound and a cecal defect in the rat following with an absorbable hyaluronic acid (hyaluronic acid)-based material.

| TREATMENT | INCIDENCE OF ADHESION FORMATION | |
|---|---|---|
| | # of animals with adhesion/ # of animals treated | % |
| NONE (CONTROLS) | 11/11 | 100 |
| HYALURONIC acid GEL (full dose) | 1/3 | 33 |
| HYALURONIC ACID GEL (half dose) | 1/5 | 20 |

With hyaluronic acid gel, 2 out of 8 animals treated developed adhesions; one in the full-dose group and one in the half-dose group. One of these adhesions only involved 4% of the wound surface and was considered to be an extremely minor adhesion (Table 1).

In contrast to the treated animals, all animals that did not receive treatment developed adhesions (Table 1). All control animals developed strong 1:1 adhesions with a mean normalized work value of 1.61+0.74 N-cm, a mean area of 1.29 cm$^2$ and a mean maximum strength 1.07 N. These adhesions involved a mean of 42% of the wound area and required a mean of 0.83 N cm to separate.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method of forming an anti-adhesion barrier comprising:

freeze-drying a solution including hyaluronic acid to form a foam;

reacting the foam with a crosslinking agent to form a crosslinked foam; and mixing the crosslinked foam with an aqueous solution containing hyaluronic acid to form an anti-adhesion barrier.

2. The method according to claim 1 wherein the concentration of the solution including hyaluronic acid is from about 0.5 to about 4.0% by weight hyaluronic acid.

3. The method according to claim 1 wherein during the freeze-drying step the solution including hyaluronic acid is frozen at a temperature of about −94 to about −130° C.

4. The method according to claim 1 wherein the solution including hyaluronic acid is freeze-dried at less than about 50×10$^{-3}$ torr and about −10° C.

5. The method according to claim 1 wherein the crosslinking agent is selected from the group consisting of di-epoxides, polyfunctional epoxides, diisocyanates, polyisocyanates, polyhydric alcohols, water-soluble carbodiimides, diaminoalkanes, diamines, polycarboxylic acids, diacid halides and dimethylol urea.

6. The method according to claim 5 wherein the crosslinking agent is a diacid halide.

7. The method according to claim 6 wherein the diacid halide is diglycolyl chloride.

8. The method according to claim 1 wherein a solution of crosslinking agent contains from about 10 to about 80% by weight crosslinking agent.

9. The method according to claim 1 wherein the proportion of foam to crosslinking agent is from about 3.0 to about 100 grams foam/gram of crosslinking agent.

10. The method according to claim 1 wherein the aqueous solution containing hyaluronic acid solution contains from about 0.5 to about 4.0% by weight hyaluronic acid.

11. The method according to claim 1 wherein the proportion of the crosslinked foam to the aqueous solution containing hyaluronic acid is from about 0.2 to about 1.0 grams crosslinked foam/ml aqueous solution containing hyaluronic acid.

12. An anti-adhesion barrier which is a gel produced by combining a freeze-dried crosslinked hyaluronic acid foam with an aqueous solution comprising hyaluronic acid.

13. The anti-adhesion barrier according to claim 12 wherein the crosslinked foam is crosslinked with a diacid halide.

14. The anti-adhesion barrier according to claim 13 wherein the diacid halide is diglycolyl chloride.

15. A composition comprising an anti-adhesion barrier according to claim 12, and a pharmaceutically acceptable carrier.

16. The composition according to claim 15 further including a medicinal agent.

17. An anti-adhesion barrier produced according to the method of claim 1.

18. The anti-adhesion barrier according to claim 17 wherein the solution including hyaluronic acid contains from about 0.5 to about 4.0% by weight hyaluronic acid.

19. The anti-adhesion barrier according to claim 17 wherein the crosslinking agent is a diacid halide.

20. The anti-adhesion barrier according to claim 19 wherein the diacid halide is diglycolyl chloride.

21. A composition comprising an antiadhesion barrier according to claim 17, and a pharmaceutically acceptable carrier.

22. The composition according to claim 21 further including a medicinal agent.

23. A method of preventing or inhibiting the formation of adhesions comprising applying an effective amount of the anti-adhesion barrier according to claim 12 to a wound site.

24. The method according to claim 23 wherein the crosslinked foam is crosslinked with diglycolyl chloride.

25. A method of promoting healing of a wound comprising applying an effective amount of the anti-adhesion barrier according to claim 12 to the wound.

26. A two-part kit comprising
a first part including a freeze-dried crosslinked hyaluronic acid foam; and a second part including a solution including hyaluronic acid.

27. The kit according to claim 26 wherein the crosslinked hyaluronic acid foam is crosslinked with a diacid halide.

28. The kit according to claim 27 wherein the diacid halide is diglycolyl chloride.

29. The kit according to claim 26 further including means for combining the crosslinked hyaluronic acid foam and the solution including hyaluronic acid.

30. The kit according to claim 26 further including a medicinal agent.

31. An anti-adhesion barrier comprising a hyaluronic acid foam, a crosslinking agent and an aqueous solution containing hyaluronic acid.

32. The anti-adhesion barrier according to claim 31 wherein the crosslinking agent is selected from the group consisting of di-epoxides, polyfunctional epoxides, diisocyanates, polyisocyanates, polyhydric alcohols, water-soluble carbodiimides, diaminoalkanes, diamines, polycarboxylic acids, diacid halides and dimethylol urea.

33. The anti-adhesion barrier according to claim 32 wherein the crosslinking agent is a diacid halide.

34. The anti-adhesion barrier according to claim 33 wherein the diacid halide is diglycolyl chloride.

35. The anti-adhesion barrier according to claim 31 wherein the solution containing hyaluronic acid contains from about 0.5 to about 4.0% by weight hyaluronic acid.

36. A composition comprising an anti-adhesion barrier according to claim 31, and a pharmaceutically acceptable carrier.

37. The composition according to claim 36 further including a medicinal agent.

* * * * *